United States Patent [19]
Bhattacharya et al.

[11] Patent Number: 4,822,825
[45] Date of Patent: Apr. 18, 1989

[54] BASE-MODIFIED ZEOLITE-CONTAINING CATALYSTS FOR THE CONVERSION OF SYNTHESIS GAS TO ALCOHOLS

[75] Inventors: Ajit K. Bhattacharya, Hopewell Junction, N.Y.; Michael S. Bolmer, Collegeville, Pa.; Guillermo Prada-Silva, Wappinger Falls, N.Y.

[73] Assignee: Texaco Inc., White Plains, N.Y.

[21] Appl. No.: 185,575

[22] Filed: Apr. 25, 1988

[51] Int. Cl.$^4$ ............................................. C07C 27/06
[52] U.S. Cl. .................................. 518/714; 518/728; 518/721; 518/717; 502/62
[58] Field of Search ................ 518/714, 728, 721, 717

[56] References Cited
U.S. PATENT DOCUMENTS 4,661,525  4/1987  Graziosi et al. ..................... 518/714
4,749,724  6/1988  Quarder et al. ..................... 518/714

Primary Examiner—Howard T. Mars
Attorney, Agent, or Firm—Robert A. Kulason; James J. O'Loughlin; Vincent A. Mallare

[57] ABSTRACT

A method for preparing a mixture of lower aliphatic alcohols from the reaction of carbon monoxide and hydrogen in the presence of a zeolite-containing heavy metal catalyst under carbon monoxide-hydrogenation conditions in which said catalysts comprises a zeolite support, at least one heavy metal oxide selected from the group of oxides consisting of molybdenum, tungsten, rhenium, optionally, a heavy metal oxide from the group of elements consisting of cobalt, iron and nickel and an alkali or alkaline earth promoter which has been treated with a nitrogen-containing compound, or a thermally stable derivative thereof is provided. A method for preparing zeolite-containing catalysts by treating with volatile metal complexes at high pressure is also provided.

6 Claims, No Drawings

BASE-MODIFIED ZEOLITE-CONTAINING CATALYSTS FOR THE CONVERSION OF SYNTHESIS GAS TO ALCOHOLS

BACKGROUND OF THE INVENTION

Field of the Invention

This invention broadly relates to a process for preparing aliphatic alcohols from synthesis gas and, more particularly, to an improved process in which a zeolite-containing heavy metal oxide catalyst is employed to effect the hydrogenation of carbon monoxide to produce a mixture of lower aliphatic alcohols. This invention also relates to a method of preparing zeolite-containing catalysts which may be useful in the above process.

Lower aliphatic alcohols have been proposed as octane enhancers or as a replacement for gasoline in fueling internal combustion engines. Certain mixtures of lower aliphatic alcohols have the EPA approval for use and are currently being marketed in the United States. The lower aliphatic alcohols can be produced from domestically available non-petroleum sources and the use of these alcohols in fuel compositions can serve to lessen the nation's dependence on foreign sources of crude oil and petroleum products.

Hydrogen and carbon monoxide or synthesis gas, a mixture of hydrogen and carbon monoxide, can be reacted to form a mixture of lower aliphatic alcohols. The synthesis gas feedstream can be produced from such non-petroleum sources as coal and biomass in well known partial oxidation reactions.

Numerous catalytic processes have been studied in attempts to provide a viable process for the production of aliphatic alcohols from synthesis gas. The early efforts were primarily directed to the production of methanol. More recently, attention has been directed to the production of higher aliphatic alcohols or a mixture of higher aliphatic alcohols with methanol. Such a mixture is highly suitable as an octane enhancing component for motor fuel and as a substitute for tetraalkyl lead additives in motor fuel.

A major problem with the synthesis gas to alcohol conversion process is the occurrence of competing reactions constantly taking place on the surface of the catalyst. Thus, even when the desired product is formed on the catalyst, some of this product may undergo further reactions with adverse effects on the yield of the desired product. It is evident that if some means could be provided for reducing or minimizing competing reactions on the catalyst surface, then improved yields of the desired product might be obtained. In accordance with this invention, a decrease in the number of surface acid sites is achieved by treatment with a thermally stable base or derivative thereof. This procedure reduces the dehydration of product alcohols on the catalyst's acid sites and this results in improved productivity and selectivity.

DISCLOSURE STATEMENT

U.S. Pat. No. 3,345,427 discloses a dehydrogenation catalyst and process in which the catalyst consists of nickel, molybdenum and alkaline metal oxides on an alumina support.

U.S. Pat. No. 4,096,164 discloses a process for reacting hydrogen and carbon monoxide in the presence of a solid catalyst comprising rhodium with molybdenum or tungsten to produce two carbon-atom oxygenated hydrocarbons in which ethanol is the major component.

U.S. Pat. Nos. 4,243,553 and 4,243,554 disclose a molybdenum disulfide catalyst that is useful in the water gas shift, methanation, hydrogenation and dehydrogenation processes. U.S. Pat. Nos. 4,607,056 and 4,607,055 disclose synthesis gas to alcohol processes in which the catalyst comprises molybdenum in combination with a metal from the group consisting of cobalt, iron and nickel in an oxide form with an alkali metal promoter.

EPA No. 0119609 discloses an alkali promoted molybdenum disulfide catalyst that is useful for producing aliphatic alcohols from synthesis gas. The disclosures of U.S. Pat. Nos. 3,345,427; 4,096,164; 4,243,553; 4,243,554; 4,607,056; 4,607,055 and EPA No. 0119609 are incorporated herein by reference.

SUMMARY OF THE INVENTION

It has been discovered that a mixture of carbon monoxide and hydrogen can be reacted in the presence of a base-treated heavy metal oxide catalyst to form a mixture of lower aliphatic alcohols. More specifically, an improved process has been discovered which employs a catalyst comprising:

(1) a zeolitic support comprising of a member selected from faujasite-type materials such as Y zeolites and X zeolites, aluminophosphates, pentasil-type molecular sieves such as ZSM-5, ZSM-11, silicalite, zeolite A and mordenite;

(2) a nitrogen-containing compound, or a thermally stable derivative thereof;

(3) at least one heavy metal oxide selected from the group comprising of molybdenum oxide, tungsten oxide and rhenium oxide, (4) optionally, a heavy metal oxide selected from the group of elements consisting of cobalt oxide, iron oxide and nickel oxide; and (5) a promoter comprising an alkali or alkaline earth element in free or combined form.

This invention also encompasses a method for improving the productivity and selectivity of a zeolite-containing heavy metal oxide catalyst for converting synthesis gas to alcohols wherein said zeolite-containing catalyst is treated with a nitrogen-containing compound or a thermally stable derivative thereof.

DETAILED EMBODIMENTS OF THE INVENTION

In accordance with this invention, synthesis gas or a mixture of carbon monoxide and hydrogen is reacted under carbon monoxide hydrogenation conditions in the presence of a catalyst comprising:

(1) a zeolitic support consisting of a member selected from the group of materials consisting of Y zeolite, X zeolite, aluminophosphate, ZSM-5, ZSM-11 silicalite, zeolite A and mordenite;

(2) a nitrogen-containing compound, or a thermally stable derivative thereof, (3) at least one heavy metal oxide selected from the group consisting of molybdenum oxide, tungsten oxide and rhenium oxide;

(4) optionally, a heavy metal oxide selected from the group comprising of cobalt oxide, iron oxide and nickel oxide; and (5) a promoter comprising an alkali or alkaline earth element in free or combined form.

The method for treating an oxide-containing heavy metal catalyst comprises forming:

(1) a zeolitic support consisting of a member selected from the group of materials consisting of Y zeolite, X zeolite, aluminophosphate, ZSM-5, ZSM-11, silicalite, zeolite A and mordenite;

(2) treating said zeolitic support with a nitrogen-containing compound or a thermally stable derivative thereof;

(3) forming at least one heavy metal oxide selected from the group consisting of molybdenum oxide, tungsten oxide and rhenium oxide;

(4) optionally forming a heavy metal oxide selected from the group consisting of cobalt oxide, iron oxide and nickel oxide; and (5) combining an alkali or an alkaline earth metal element in free or combined form with said treated metal oxide or oxides.

In a more specific aspect of the invention, a NaY zeolite support is treated with a nitrogen-containing base, such as melamine or a thermally stable derivative thereof such as melem or melon.

Synthesis gas or a mixture of hydrogen and carbon monoxide employed in this process can be obtained by methods well known in the art. The two gas components can be provided separately and combined for the reaction or the two components can be generated simultaneously in a synthesis gas process such as a coal gasification process. The feed gas to the alcohol process may employ the hydrogen to carbon monoxide in amounts broadly ranging from bout 1 to about 20 moles of hydrogen per mole of carbon monoxide. The preferred mole ratio for alcohol production is from about 1 to about 5 moles of hydrogen per mole of carbon monoxide.

Heavy metal oxide catalysts suitable for the synthesis gas to alcohols process can be prepared in a number of ways. The catalyst composition may be prepared in bulk, that is, without a catalyst support or carrier. It is also common to prepare catalyst compositions using a support for the active metal components. When such a catalyst support or carrier is employed it may comprise a relatively refractory, porous, absorptive high surface area material. Conventional catalyst supports comprise materials such as alumina, silica, titania, magnesia, silica-alumina and lanthana. Catalysts comprising the noted support materials are disclosed in U.S. Pat. No. 4,098,683 and this patent is incorporated herein by reference.

A nitrogen-containing heavy metal oxide catalyst may be prepared by treating the zeolitic support with appropriate nitrogen-containing compounds. A wide variety of nitrogen compounds may be employed in the catalyst preparation. The nitrogen compound may be selected from the group consisting of urea, dimethylolurea, cyanuric acid, melamine, melam, melem or melon with melamine being preferred.

According to the present invention, a nitrogen-containing starting material may be a monomer or a dimeric, trimeric or polymeric condensation product. Structural features such as s-triazine (I) and tri-s-triazine (II) are preferred. For example:

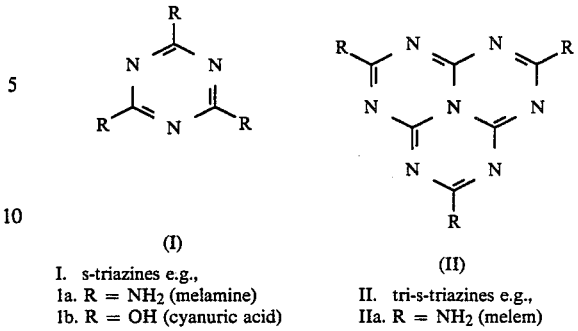

I. s-triazines e.g.,
Ia. R = NH$_2$ (melamine)
Ib. R = OH (cyanuric acid)

II. tri-s-triazines e.g.,
IIa. R = NH$_2$ (melem)

The chemistry of s-triazines and derivatives has been presented in great detail in The Chemistry of Heterocyclic Compounds, Vol. 13, E. M. Smolin and L. Rapoport, Interscience Publishers Inc. (1967) and is incorporated herein by reference.

When heated above its melting point in the absence of ammonia, melamine (mp 354° C.) decomposes with loss of ammonia to afford melam (III), melem (IIa) and melon.

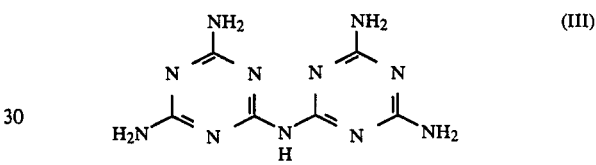

"In melamine deammonation, melam is formed first by loss of an equivalent of ammonia from two molecules of melamine. Melem is usually found together with melam and is possibly the end product of a rearrangement of melam (III).

Heating the reaction mixture at 600° C. causes further loss of ammonia with the formation of melon, a compound, or rather substance which can survive red heat."

For the process of the present invention, a zeolitic support is treated with a nitrogen-containing compound at an intermediate point in the preparation of the catalyst. Alternatively, a Co/Mo/zeolite catalyst precursor can be treated prior to addition of the alkali/alkaline earth component. Samples are treated with an aqueous solution of nitrogen-containing compound, preferably a base such as melamine. Treating is effected using a relatively dilute, aqueous solution of the nitrogen compound. In general, the aqueous preparation may contain from about 0.1 to about 20 wt.% of the nitrogen-containing compound with a concentration from about 0.5 to about 10 wt.% being preferred.

The mixture of the zeolitic support and the aqueous nitrogen-containing compound are thoroughly mixed to incorporate the nitrogen-containing compound onto the support. Continuous stirring while the mixture is maintained at a moderately elevated temperature from about 50° to about 60° C. for an hour or for several hours has been found effective. The treated zeolitic support is then separated from the mixture by filtration and dried under a vacuum. Subsequently, the treated zeolitic support is subjected to calcination. In general, calcination is effected at an elevated temperature ranging from about 300° to about 700° C. while under an inert atmosphere. A preferred calcination temperature range is from about 400° to about 600° C. It is preferred to conduct the calcination while passing a stream of inert gas, such as nitrogen, over the catalyst.

Following calcination, the base-treated zeolite is combined with the prescribed heavy metals by treating with volatile molybdenum and cobalt complexes at such pressure and temperature that the complexes are below their decomposition temperature. It is preferable (1) to perform the preparation at a temperature above the sublimation or boiling temperature of the molybdenum and cobalt complexes, (2) to suspend the base-treated zeolite in an inert liquid to obtain uniform temperature and concentration and to (3) use a liquid whose molecular size is larger than the pores of the zeolite support so that it will not block the pores and interfere with loading of the heavy metals. Alternatively, molybdenum and cobalt may be combined with the support by procedures well known in the art such as impregnation, although impregnation will probably result in lower metal dispersions. Finally, addition of the alkali promoter is effected by ion exchange in an aqueous solution of an alkali salt. The catalyst is then washed with water and acetone and dried in a vacuum oven at 120° C.

The final catalyst composition for the process of the invention may contain an amount of the thermally stable nitrogen-containing compound that will provide from about 0.01 to about 20 wt.% of nitrogen, calculated as N, based on the total weight of the catalyst. A preferred concentration of this component is from bout 0.05 to about 10.0 wt.%.

In addition to the nitrogen, the final catalyst composition may contain from about 0.3 to about 15 wt.% of molybdenum calculated as $MoO_3$, from about 0.5 to about 20 wt.% cobalt calculated as CoO and from about 2 to about 25 wt.% of an alkali metal selected from the group consisting of potassium, cesium and rhubidium. THe balance of the catalyst consisting of a support such as base-modified zeolite Y.

The following Example illustrate applicants' novel process based on the use of a zeolite-containing heavy metal oxide catalyst which has been treated with a nitrogen-containing compound.

EXAMPLE I

A 1 percent melamine solution is prepared by dissolving 2.5 gr of melamine in enough deionized water to make up 250 ml of solution. The solution is heated to 50° C. and 50 grams of NaY zeolite (pore size 7.4 A) are suspended while stirring for one hour. The sample is filtered and dried under reduced pressure at 120° C. The material is then heated at 400° C. for one hour under nitrogen flow.

Twenty grams of this product are put into a glass liner under nitrogen atomsphere along with 20 gr Mo(CO)$_6$, 5 gr Co$_2$(CO)$_8$ and 200 ml perfluorotributylamine (molecular size 10.2 A). The glass liner is placed in a rocker bomb and pressurized to 2000 psig with carbon monoxide. The contents are heated to 100° C. and this temperature maintained for two hours. After cooling, the pressure is released, the material is filtered and subsequently washed with 200 ml of hexane and 1800 ml of water.

Finally, alkali is ion-exchanged by placing 55 gms of this damp product in a beaker with 1500 ml of water and 11 gr of potassium carbonate, stirring at 80° C. for one hour. The material is then filtered and washed with 500 ml of water. After repeating this ion-exchange procedure, the catalyst is dried in a vacuum oven at 120° C.

The chemical composition of a catalyst (Sample B) prepared according to the above procedure is as follows:

$Co_{22.2}Mo_{6.7}K_{52}Na_{15}C_{21}N_{14}Al_{53}Si_{139}O_{384}$

It should be noted that the sum of K and Na equals the sum of N and Al. This suggests that the base sites incorporated in the catalyst can hold additional alkali-promoter ions and, thus, increase productivity to alcohols.

The effectiveness of the catalysts of this invention is converting a mixture of carbon monoxide and hydrogen to a mixture of lower aliphatic alcohols was tested in a fixed bed microreactor. One quarter of a gram of catalyst was mixed with 2.25 gr of alpha-alumina. Hydrogen and carbon monoxide, at a ratio of 2:1, was passed through the catalyst bed at a space velocity of 48,000 hr, a temperature of 327° C. and a pressure of 1400 psig. Results comparing the performance of a base-modified zeolite-containing catalyst (Sample B) to that of a standard catalyst (Sample A) of chemical composition

$Co_{7.4}Mo_{7.6}K_{44}Na_9Al_{53}Si_{139}O_{384}$ are presented below in Table I.

TABLE I
EFFECT OF BASE MODIFICATION ON ZEOLITE-CONTAINING CAALYSTS

|  | Standard Sample A | Base-Modified Sample B |
|---|---|---|
| CO conversion, % | 3 | 34 |
| C$_1$OH productivity g/g-hr | 0.16 | 0.69 |
| C$_2$+ OH productivity g/g-hr | 0.01 | 0.65 |
| C$_1$OH selectivity, % (CO$_2$-free basis) | 31 | 11 |
| C$_2$+ OH selectivity, % (CO$_2$-free basis) | 2 | 17 |

The above data show that when melamine is used to modify the acid properties of zeolite-containing catalysts, considerable increases are obtained in the conversion of carbon monoxide, the alcohol productivity and the selectivity to higher alcohols.

We claim:

1. In a method for preparing lower aliphatic alcohols which comprises reacting carbon monoxide and hydrogen in the presence of a zeolite-containing heavy metal oxide catalyst under carbon monoxide-hydrogenation conditions, said catalyst comprising:
   (a) a zeolite support consisting of a member selected from the group consisting of Y zeolite, X zeolite, aluminophosphate, ZSM-5, ZSM-11, silicalite, zeolite A and mordenite;
   (b) at least one heavy metal oxide selected from the group consisting of molybdenum oxide, tungsten oxide and rhenium oxide;
   (c) optionally a heavy metal oxide from the group of elements consisting of cobalt oxide, iron oxide and nickel oxide; and
   (d) a promoter comprising an alkali or alkaline earth element in free or combined form;
the improvement which comprises improving the selectivity to said alcohols by treating said zeolite support with a nitrogen-containing base selected from the group consisting of urea, dimetholurea, cyanuric acid, melamine, melan, melem and melon.

2. The method according to claim 1 in which said nitrogen-containing compound is melamine.

3. The method according to claim 1 in which said nitrogen-containing compound is melam.

4. The method according to claim 1 in which said nitrogen-containing compound is melem.

5. The method according to claim 1 in which said nitrogen-containing compound is melon.

6. The method according to claim 1 in which said catalyst contains from about 0.01 to about 10 wt.% nitrogen, calculated as N, from about 0.3 to about 15 wt.% molybdenum, calculated as $MoO_3$, from about 0.5 to about 20 wt.% cobalt, calculated as CoO and from about 2 to about 25 wt.% of an alkali metal selected from the group consisting of potassium, cesium and rhubidium and the balance consisting of a support such as NaY zeolite.

* * * * *